United States Patent [19]

Dobbs

[11] Patent Number: 4,758,162
[45] Date of Patent: Jul. 19, 1988

[54] DEVICE AND METHOD FOR THE PREPARATION OF A FIXED DENTAL BRIDGE

[76] Inventor: Charles T. Dobbs, 18383 Van Rd., Livonia, Mich. 48152

[21] Appl. No.: 928,814

[22] Filed: Nov. 7, 1986

[51] Int. Cl.⁴ .............................................. A61C 11/00
[52] U.S. Cl. ................................. 433/213; 433/181; 433/191
[58] Field of Search .............. 433/213, 180, 181, 182, 433/183, 191, 192, 193

[56] References Cited

U.S. PATENT DOCUMENTS

| 911,398 | 2/1909 | Ivory | 433/192 |
| 2,213,963 | 9/1940 | Myerson | 433/191 |
| 2,213,964 | 9/1940 | Myerson | 433/192 |
| 2,700,184 | 1/1955 | Levine | 433/213 |
| 2,826,814 | 3/1958 | Sappey et al. | 433/193 |
| 4,269,595 | 5/1981 | Nemethy | 433/191 |

FOREIGN PATENT DOCUMENTS 619856  10/1980  Switzerland ...................... 433/191

*Primary Examiner*—John J. Wilson
*Attorney, Agent, or Firm*—Arnold S. Weintraub

[57] ABSTRACT

An apparatus for the preparation of a fixed bridge which includes a wax occlusal bar adapted to be positioned within a gap located between two abutments in a model of the patient's mouth and at least one removable wax pontic adapted to be carried on the occlusal bar. The wax pontic is movable and rotatable relative to the bar. The method of preparing a wax bridge employing this apparatus includes the following steps:

(a) preparing a model of the patient's mouth;
(b) inserting an occlusal bar into a gap between the two teeth;
(c) temporarily affixing the bar in the gap;
(d) movably positioning at least one pontic on the occlusal bar;
(e) affixing the positioned pontic to the occlusal bar; and
(f) removing the occlusal bar with the pontic affixed thereto from the model. The prepared wax bridge can then be used to cast a suitable fixed bridge.

12 Claims, 2 Drawing Sheets

DEVICE AND METHOD FOR THE PREPARATION OF A FIXED DENTAL BRIDGE

BACKGROUND OF THE INVENTION

1. Field of the Invention

This invention relates to devices and methods for making fixed dental bridges. More specifically, this invention relates to methods and devices for making fixed bridges which involve the use of lost wax techniques.

2. Background of the Prior Art

Tooth loss due to decay, injury or the like can necessitate the need for replacement using fixed bridges. A fixed bridge is a tooth or series of teeth anchored to existing healthy teeth to replace and fill gaps or omissions in the patient's mouth. The replacement teeth can be constructed of porcelain, inert metals, or mixtures of the two.

The preferred method of producing a fixed bridge involves the use of a "lost wax" technique. The lost wax technique is well known in the art. In a lost wax casting, a wax form resembling the tooth or teeth to be cast in prepared and positioned. A mold is formed around the wax. A molten material such as an inert metal is poured into the mold, melting the wax as it enters. The molten material is permitted to solidify after which the mold is opened leaving a casting of the appropriate tooth shapes. Procelain or other aesthetic material can, then, be applied to the outer suface of the metal casting to provide an aesthetically pleasing surface which resembles natural teeth. Various methods have been proposed for the manufacture and installation of the wax bridge or pre-mold. Most of these methods involve taking an impression of the patient's mouth, and preparing a cast model from the impression. The gaps caused by missing teeth can, then, be filled with appropriate wax sculpted members. These members can, then, be used to form a mold to cast the fixed bridge.

To date, there are two methods of constructing the wax pre-molds. The older method involves individual sculpting of a wax plug into the appropriate tooth shapes. This method requires a great deal of artistry and talent to ensure that the tooth shapes prepared will be properly oriented and will yield suitable cast members. The second method involves the use of individual wax tooth shapes or pontics. The individual pontics must be placed in position in the appropriate gap and held while they are molded together. This method is incredibly tedious and prone to error as each pontic must be individually positioned with respect to tooth height, tooth spacing and orientation in opposition to the opposed jaw member.

It is to be understood that the pontics must be specifically oriented to ensure an appropriate bite. This means that the pontic must be positioned precisely in relation to the existing teeth on either side of it and must also have correct cusp to fossa relationship. Any variance will cause an incorrect bite and can, potentially, damage the surrounding or opposing teeth. Because of the precise positional requirements, the individuals preparing the wax casting for the fixed bridge must be highly skilled. Even so, the opportunity for error and mistake is great.

Thus, it would be desirable to provide a device and method for preparing the wax pre-casting in which the individual pontics could be readily adjusted for gap, orientation and the like. It is also desirable that a method and device be provided which will permit accurate orientation of the individual pontics with no undue experimentation or manipulation.

SUMMARY OF THE INVENTION

There is disclosed in the present invention an apparatus for preparing a pre-cast member for casting a fixed bridge. Also disclosed in the present invention is a method for preparing a fixed bridge using the present apparatus.

The apparatus for preparing a pre-casting member for casting a fixed bridge of the present invention comprises a wax occlusal bar having a longitudinal axis and at least one wax pontic adapted to be carried on the occlusal bar, movable along said bar and rotatable about said longitudinal axis. The apparatus of the present invention is used in connection with a cast model of a patient's mouth. The cast model would be prepared and oriented to show any gaps caused by the loss of the patient's teeth, as well as the orientation of the upper and lower jaws and associated teeth.

In using the present invention, the wax occlusal bar is adapted to positioned within a gap located between two abutments in the model such that the longitudinal axis of the occlusal bar is essentially perpendicular to the two abutments. It is to be understood that these abutments can be existing teeth which are usually prepared to receive a crown or other anchoring means which can be attached to the fixed bridge, or other suitable members fixed within the mouth of the patient.

The wax pontics carried on the occlusal bar have a configuration similar to cuspids, bicuspids, molars or other teeth. The choice of pontic employed depends upon the desired location of the fixed bridge within the mouth of the patient.

The method of the present invention comprises the following steps:

(a) preparing a model of a patient's mouth including the gap in which the fixed bridge is to be attached;

(b) inserting an occlusal bar having a longitudinal axis and two respective ends into position within the gap between two opposing abutments;

(c) temporarily affixing the respective ends of the occlusal bar to an associated abutment;

(d) movably positioning at least one pontic on the occlusal bar;

(e) placing the pontic in the desired orientation;

(f) affixing the pontic to the occlusal bar to form a wax fixed bridge; and (g) removing the prepared wax fixed bridge bar from the model.

The wax bridge is thus prepared for casting in the conventional manner.

DESCRIPTION OF THE DRAWING

For a fuller understanding of the nature and object of the invention, reference should be made to the following detailed description taken in connection with the accompanying drawings in which.

DESCRIPTION OF THE PREFERRED EMBODIMENT

It is to be understood that the apparatus and method of the present invention can be employed to produce a fixed bridge of varying size in either the upper or lower mouth.

To prepare a patient for a bridge, the dentist performs any necessary oral surgery or other preparation. This can include any conventionally known tecniques which will facilitate later placement and anchoring of the bridge in the mouth of the patient.

After the required extractions and cutting down procedures, an impression of the patient's mouth contours is taken from which a suitable positive casting of the dental impressions is prepared. The apparatus of the present invention is adapted to be inserted in or used in conjunction with suitable castings. Vacant spaces or gaps located on the cast replica represent extracted teeth.

Figure 2A:
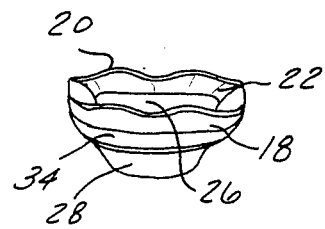
FIGS. 2a and 2b are lingual views of two pontics constructed in accordance with the present invention.
Figure 2:
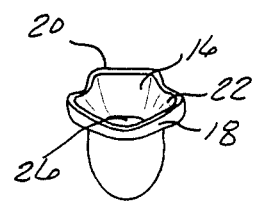
Figure 3A:
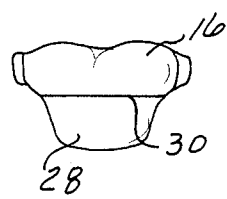
FIGS. 3a and 3b are buccal views of two pontics constructed according to the present invention.
Figure 3B:
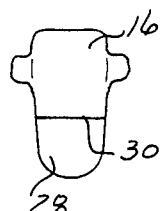
Figure 4A:
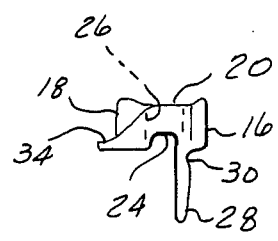
FIGS. 4a and 4b are mesial views of two pontics constructed according to the present invention.
Figure 4B:
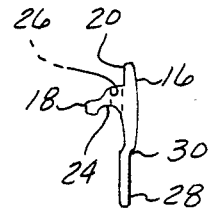

The apparatus of the present invention comprises a wax occlusal bar 12 and at least one movable wax pontic 14. The wax occlusal bar 12 can be of any suitable width or gauge. In the preferred embodiment, a 12-gauge bar is used. The movable pontic is a pre-cast wax miniature of the missing tooth. In the preferred embodiment, the pontic chosen is a reduced dimension replica of the final product desired. The wax pontic has the contour of the final product desired. Representative pontics constructed according to the present invention are shown in detail in FIG. 2a and FIG. 2b which show a molar pontic and an anterior pontic in lingual view. Buccal views of the same pontics are depicted in FIGS. 3a and 3b. Side views of the same pontic are shown in FIGS. 4a and 4b. While the configuration of the various pontics may differ, each pontic has a buccal member 16, a lingual member 18 and an occlusal member 20 located between and connecting the buccal member 16 with the lingual member 18. The occlusal member 20 has an upper surface 22 which is directed toward the direction of the clamping or biting force. The buccal member 16, lingual member 18 and occlusal member 20 of each pontic cooperate to form a slot 24 (shown most clearly in FIGS. 4a and 4b) adapted for receiving the occlusal bar. The slot is opposed to the occlusal face 22 and is essentially parallel to the buccal member 16.

In the preferred embodiment, each pontic 14 has an aperture 26 centrally located within the occlusal member 20. The aperture 26 is adapted for securing the pontic 14 to the occlusal bar 12 in a manner which will be described in greater detail hereafter. Additionally, it has been found that the presence of the aperture 26 will provide contours which permit greater adhesion characteristics between the metal casting obtained from this wax pre-cast and any overlayment of porcelain which may be desired.

In the preferred embodiment, the buccal member 26 of each pontic 14 can also be provided with a projection 28 and a score line 30. The projection 28 extends outward in a direction opposed to the occlusal surface 22. The projection 28 aids in the orientation of the pontic 14 on the occlusal bar 12 in a manner which will be described in greater detail subsequently. After the pontic 14 has been suitably oriented, the projection 28 can be removed by cutting or severing it from the remaining buccal member 16 at the score line 30.

In the preferred embodiment, the lingual member 18 of each pontic also has an outwardly projecting ledge 34. The outwardly projecting ledge 34 is located on the lingual member 18 at a position generally opposed to the slot 24. The presence of the outwardly projection ledge 34 permits the formation of a shelf when the fixed bridge is cast. The shelf permits greater adhesion between the metal substrate and any porcelain or aesthetic coating applied over the top of it. Additionally, the presence of the ledge 34 assists in the positioning of the pontic 14 of the occlusal bar in a manner which will be described subsequently.

Figure 5:
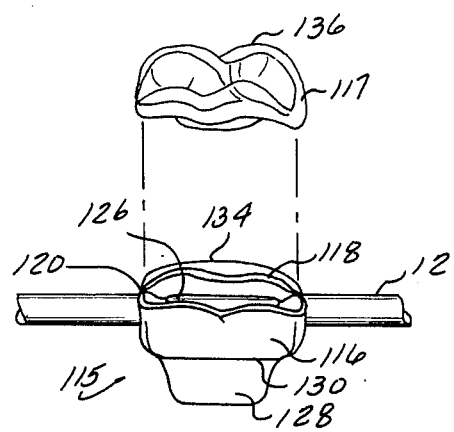
FIG. 5 is a perpective view of a two-piece pontic constructed according to the present invention.
Figure 6:
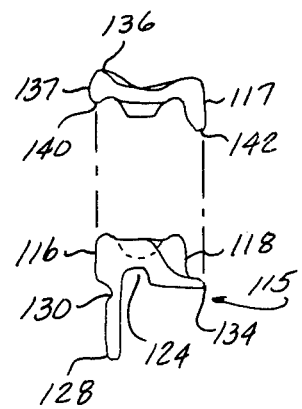
FIG. 6 is a side view of a two-piece pontic of the present invention.

It is also within the purview of this invention to provide two-piece pontics 114; such as is illustrated in FIGS. 5 and 6. The two-piece pontic 114 consists of an anchoring member 115 and a crown member 117. The anchoring member 115 is adapted to be positioned on the occlusal bar 12. The anchoring member 115 comprises a buccal member 116, a lingual member 118, and an occlusal member 120 similar to those described previously in connection with pontic 14. The buccal member 116, lingual member 118, and occlusal member 120 cooperate to form an occlusal surface 122 and a slot 124. The slot 124 is adapted to receive the occlusal bar 12 in the manner described previously. An aperture 126 is centrally located in the occlusal member 120. The anchoring member 115 can also, optionally, have a projection 128 and a score line 130. Also optionally present on the anchoring member 15 is a ledge 134 located on the lingual member 118. The ledge 134 and the projection 128 function in the manner previously described with respect to pontic 14.

The crown member 117 of the two-piece pontic 114 consists of an outer occlusal surface 136 and an inner engaging surface 137. The inner engaging surface is configured to be matingly received on the occlusal member 120. The inner mating surface 137 can be appropriate projections 140 which can extend into aperture 126 to provide a secure and mating fit between the anchoring member 115 and the crown member 117. The outer biting surface 136 of the crown member 117 is, preferably, configured in the shape of the surface of a conventional molar.

As can be best seen in FIG. 6, the crown member 117 has an elongated lip 142 which matingly corresponds to the size and shape of lingual member 118 of the anchoring member 115. The foremost edge of the elongated lip 142 is adapted to contact the ledge 134 of the anchoring member 115. The surface of the crown member 117 opposed to the elongated lip 142 corresponds with the uppermost surface of the buccal member 116.

This two-piece configuration permits separate casting of the lower portion or anchoring member 115 independently as part of the fixed bridge.

In using the pre-casting apparatus of the present invention, a model of the patient's mouth is prepared in a conventional manner. Once the model is prepared, an occlusal bar 12 of suitable lengths can be inserted in the gap for which a fixed bridge is desired. The occlusal bar is preferably a 12-gauge wax wire and is cylindrical with a diameter between about 2½ to 3 millimeters. The occlusal bar employed has sufficient flexibility for bending conformation with the ridge of the patient's mouth.

Figure 1:
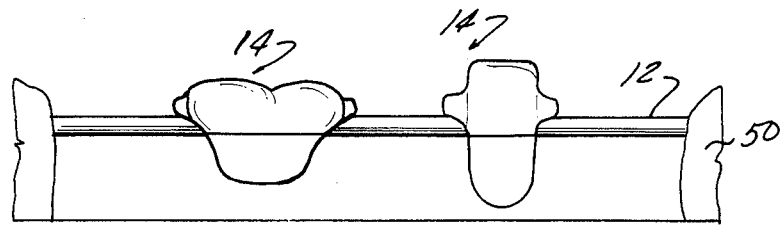
FIG. 1 is a side view of a wax bridge made by the method of the present invention.

The occlusal bar 12 is placed between abutment 50 in the manner shown in FIG. 1. The abutment 50 has been prepared to receive a crown attached to the fixed bridge in a conventional manner. The crown maintains the bridge in position in the patient's mouth. It is to be understood that other anchoring methods can be employed using the teaching of the present invention, i.e., Maryland bridge, retentive wings, etc..

Placement of the occlusal bar is strictly regulated to give the proper cusp to fossa relationship shown in detail in FIG. 5 to assure proper bite and wearing comfort. FIG. 5 demonstrates a pair of opposing fixed bridges for at least one upper molar. The occlusal bar 12 is oriented such that the center of the occlusal bar is directly parallel with the cusp C of the lower tooth. By careful orientation in this manner, the cusp C of the lower tooth will smoothly mesh with the fossa F of the finished replacement bridge tooth.

Once the occlusal bar 12 is in position, it can be held in place by affixing the two respective ends of the occlusal bar to the associated abutment 50, 50'. This is preferably accomplished by use of a sticking wax between the ends of the occlusal bar 12 and the associated abutment 50, 50'.

As necessary, the bar may be slightly bent or deformed to provide conformance with the underlying ridge of the patient's jaw bone. Once the occlusal bar is affixed in the appropriate position, the desired pontics 14, 14' can be movably positioned on the bar. It is to be understood that the type of pontic chosen is that which is desired for the position of the mouth. Anterior pontics would generally have the configuration shown in FIGS. 2b, 3b and 4b; while posterior pontics would have a biscuspid or molar configuration such as is shown in FIGS. 2a, 3a, 4a or FIG. 5. The pontics can be slid horizontally along the occlusal bar 12 to ensure proper alignment with corresponding teeth on the opposed jaw. Once the vertical alignment is ascertained, the pontic can be axially rotated along the jaw to ensure appropriate cusp to fossa mating. In rotation and movement, the builder can easily move the downwardly oriented projection 28, 128 and the ledge 34, 134 to permit minute changes in the axial orientation.

Once appropriate orientation has been achieved, a minute amount of wax can be inserted in the aperture 26, 126 or along the interior ledge 34, 134 to secure the pontic to the wax occlusal bar. The procedure can be repeated for any other pontics inserted on the bar. The occlusal bar and abutments with attached pontics can, then, be removed from the model and used to prepare a mold for conventional casting procedures.

When a two-piece pontic 114 is employed, the anchoring member 115 is attached to the occlusal bar 12 in the manner just described. Depending upon the type of finish desired on the molar-type tooth, the crown member 17 can then be attached to the anchoring member 115 and cast. The two-piece pontic 114 can be used to eliminate the need for free-hand waxing.

In this manner, a wax bridge suitable for manufacture of a fixed bridge can be easily and efficiently made.

Having thus described the apparatus and method of the present invention, what is claimed is:

1. An apparatus for preparing a pre-casting member in a model of a patient's mouth for casting a fixed bridge, the apparatus comprising:
   a wax occlusal bar having a longitudinal axis adapted to be positioned within a gap located between two abutments in the model such that the longitudinal axis of the occlusal bar is essentially perpendicular to the abutments; and
   at least one removable wax pontic the pontic including means for mounting the pontic on the occlusal bar, the pontic being movable along said bar and rotatable about said longitudinal axis.

2. The apparatus of claim 1 wherein the occlusal bar is cylindrical.

3. The apparatus of claim 1 wherein the pontic has a buccal member, a lingual member and an occlusal member connecting the buccal member and the lingual member, the pontic having an occlusal face formed on the surface of the occlusal member and a slot for receiving the occlusal bar, the slot opposed to the occlusal face and essentially parallel to the buccal member, the slot defining the means for mounting 4. The apparatus of claim 3 wherein the occlusal member has an aperture centrally located therein.

5. The apparatus of claim 3 wherein the pontic further comprises a downwardly oriented projection located on the buccal member.

6. The apparatus of claim 5 wherein the pontic further comprises a score line located on the buccal member.

7. The apparatus of claim 3 wherein the pontic further comprises an outwardly projecting ledge located on the lingual member, at a position generally opposed to the slot.

8. The apparatus of claim 7 wherein the pontic further comprises a separable crown member adapted to overlay the occlusal member, the crown member having an upper face, a central projection opposed to the upper surface, and an elongated lip with a lowermost edge parallel the central projection, the central projection adapted to matingly fit within the aperture of the pontic and the elongated lip adapted to overlay the lingual member of the pontic and the lowermost edge to engage the ledge of the pontic.

9. A method for preparing a wax bridge comprising the steps of:
   preparing a model of a patient's mouth;
   inserting an occlusal bar having a longitudinal axis and two ends into position within a gap between two teeth on the model in a position essentially perpendicular to the two teeth;
   temporarily affixing the two respective ends of the occlusal bar to an associated tooth abutment adjacent to the gap;
   mounting for rotational and longitudinal movement at least one pontic having a central occlusal fossa on the occlusal bar, positioning the at least one pontic on the occlusal bar;
   affixing the positioned pontic to the occlusal bar; and
   removing the occlusal bar with the pontic affixed thereto from the model.

10. The method of claim 9 further comprising the step of bending the bar to correspond to the curvature of the model of the patient's mouth prior to temporarily affixing the occlusal bar.

11. The method of claim 9 wherein the longitudinal axis of the occlusal bar is located in a vertical plane defined by the cusp of teeth located in the opposing jaw of the model of the patient's mouth.

12. The method of claim 9 wherein the positioning step includes:
   sliding the pontic longitudinally along the occlusal bar to a position in the same vertical plane as an associated opposing tooth; and
   rotating the pontic about the longitudinal axis of the occlusal bar to align central occlusal fossa of the pontic with an associated cusp of an opposing tooth.

* * * * *